United States Patent [19]

Stulen et al.

[11] Patent Number: 5,836,693
[45] Date of Patent: Nov. 17, 1998

[54] METHOD AND APPARATUS FOR MEASURING PRESSURE IN A PIPELINE WITHOUT TAPPING

[75] Inventors: Foster B. Stulen, Galena; Susan T. Brown, Dublin; Glenda S. Holderbaum, Hilliard; David B. Philips, Bexley; Arthur C. Eberle, Upper Arlington, all of Ohio

[73] Assignee: Columbia Gas of Ohio, Inc., Columbus, Ohio

[21] Appl. No.: 606,410

[22] Filed: Feb. 23, 1996

Related U.S. Application Data

[62] Division of Ser. No. 262,696, Jun. 20, 1994, Pat. No. 5,645,348.
[51] Int. Cl.[6] .......................... G01N 25/00; G01N 13/02; G01N 1/68
[52] U.S. Cl. .............................. 374/45; 374/138; 75/295; 75/202.5; 75/204.11
[58] Field of Search .................... 374/45, 54, 137, 374/138, 166; 73/295, 714, 753, 202.5, 204.12, 204.16, 204.17, 204.19, 204.22, 204.11, 204.23, 204.27, 861

[56] References Cited

U.S. PATENT DOCUMENTS

| | | | |
|---|---|---|---|
| 3,196,679 | 7/1965 | Howland | 73/204.11 |
| 4,187,718 | 2/1980 | Shibasaki. | |
| 4,886,370 | 12/1989 | Koshihara et al. | 374/5 |
| 5,036,701 | 8/1991 | Van Der Graaf | 73/204.12 |
| 5,209,115 | 5/1993 | Bond | 73/295 |
| 5,237,866 | 8/1993 | Nijdam | 73/204.11 |

FOREIGN PATENT DOCUMENTS

| | | | |
|---|---|---|---|
| 1195026 | 11/1959 | France | 73/204.12 |
| 58-86417 | 5/1983 | Japan | 73/204.11 |
| 59-105521 | 6/1984 | Japan | 73/202.5 |
| 5-107094 | 4/1993 | Japan | 73/204.11 |

Primary Examiner—William A. Cuchlinski, Jr.
Assistant Examiner—Andrew Hirshfeld
Attorney, Agent, or Firm—Sidney W. Millard; Kremblas, Foster Millard & Pollick

[57] ABSTRACT

A fluid-filled pipe is investigated by a nonintrusive procedure to determine whether the fluid is liquid or gaseous, whether it is flowing or static, the direction of flow if it is flowing, the approximate pressure if it is a gas, and the rate of flow if it is a gas. The results are obtained by applying a heater to the surface of the pipeline and measuring the upstream and downstream temperatures of the surface of the pipe wall before and after the beginning of the application of heat. Some of the data generated is compared with data from another source to assist in the determination of the physical characteristics to be ascertained.

4 Claims, 10 Drawing Sheets

METHOD AND APPARATUS FOR MEASURING PRESSURE IN A PIPELINE WITHOUT TAPPING

This is a division of application No. 08/262,696, filed Jun. 20, 1994, now U.S. Pat. No. 5,645,348.

FIELD OF THE INVENTION

This invention relates to a method and apparatus for determining physical characteristics of a fluid inside a pipeline without breaching the surface of the pipeline.

BACKGROUND OF THE INVENTION

This invention came about as a result of public utilities' need to know the characteristics of the contents of pipelines which may be excavated by repair crews.

Various techniques have been used by public utilities to provide later identification of specific pipe systems after they are installed and buried. The problem is, nature is not particularly cooperative in maintaining the schemes of identification originated by man.

Survey crews and draftsmen are often quite specific in preparing crossing locations for buried conduits and they are more than adequately related to landmarks available at the time the pipe is buried. Unfortunately, the street curbline may be changed by the city, the centerline of the street may be changed by the government entity responsible for maintenance, the alignment of power lines between power poles may be shifted, other pipelines or electrical conduits may be buried above or below the critical pipeline or installed at an angle crossing the same.

The problem created is one to be solved by an excavation crew on-site. It is critical for the safety of working crews and citizens near the site of an excavation for the operating crew to know the characteristics of the contents of pipelines.

For example, an excavation crew from a natural gas public utility working in an urban area will believe that it knows about where a particular pipeline is located. This information will be based on data collected from the engineering department of the utility in question. The problem is that the on-site excavation crew may find the wrong pipe and not know it. The potential for disaster is self-evident if the crew thinks that the excavated pipe is a water pipe and it turns out to be a natural gas transmission line operating at 150 psi and flowing at 25 ft/sec.

There is a need in the utility industry for an apparatus and procedure for determining physical characteristics of the fluid inside a pipeline without breaching the sidewall of the pipe. Such data would ensure that the excavation crew is operating on the right pipeline and in addition will take the necessary precautions for safety of the population when the pressure flow rate and direction of flow are available prior to the time the intended structural modifications are made to the pipeline.

SUMMARY OF THE INVENTION

Certain generalities and experimental data referred to subsequently come from experimental data involving carbon steel pipes which meet all the requirements of API 5L Schedule 40 specifications. Such generalities involve pipes ranging from 2 to 12 inches in diameter and having a sidewall thickness in the range from 0.156 to 0.375 inches. These are standard thicknesses. It will be quite obvious that the inventive concepts defined herein are applicable to a wider range of sidewall thicknesses and diameters than the standard thicknesses and diameters enumerated above and specified in industry standards.

A technique for achieving the desired result of determining physical characteristics of the fluid content of a just-excavated pipeline is accomplished by heat-transfer characteristics of various fluids at diverse pressures and under static or flowing conditions.

The apparatus of this invention involves a heater applied to the surface of the pipeline combined with a plurality of temperature-sensing devices located at the site of the heat application to the pipe surface and various locations axially transverse to the location for the application of heat.

The general inventive characteristics are applicable both to a ring-type heater extending completely around the circumference of the excavated pipe and a patch-type heater applied to the surface of the pipe which extends less than the full circumference of the pipe. It is anticipated that the patch-type heater will be the preferred apparatus for use in the field because it is smaller in size and less cumbersome to use.

The basic concept involves mounting the heater and the transversely located sensing devices on the pipeline, measuring the temperature of the pipeline surface and then applying heat at the heat source while measuring the temperature changes at the site of the heat source and the transverse locations. The pattern of heat transfer or temperature pattern allows the evaluation of the physical characteristics of the contents of the pipeline.

The ways to interpret the data generated will be described in more detail subsequently. Objects of the invention not understood from the above will become clear upon a review of the drawings and the description of the preferred embodiments which follow.

DESCRIPTION OF THE PREFERRED EMBODIMENTS

For purposes of this invention, the broad concepts are to be stated relatively simply because, after the inventive concepts were conceived and the experimental data generated to prove the same, the inventive concepts proved to be relatively straight-forward.

Figure 1:
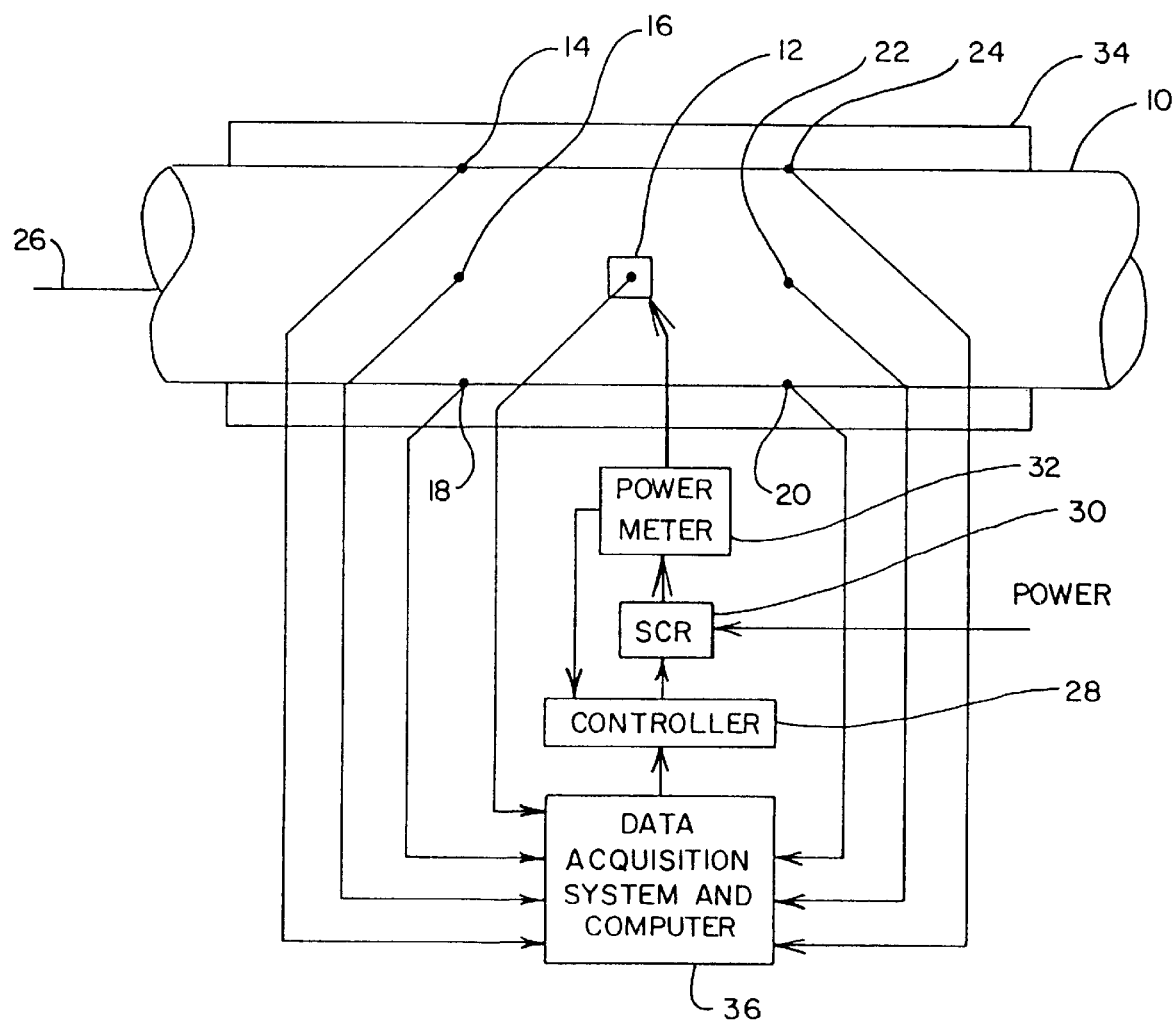
FIG. 1 is a fragmentary schematic view of an excavated pipeline with the apparatus of this invention mounted in operative position.

At the outset, a pipe 10 as shown in FIG. 1 is excavated. The excavation crew hopes it knows what is inside the pipe but its collective intuition must be verified with apparatus and procedural steps to confirm the intuitive conclusion.

A heater 12 is attached to the surface of the pipe. FIG. 1 illustrates the heater 12 as being a patch extending considerably less than completely around the circumference of the pipe. A heater of larger proportions could be used including a completely annular heater extending completely around the pipe. Experiments have indicated that a rectangular patch heater one inch by two inches is adequate.

The first determination which may be made relatively quickly is achieved by applying temperature sensors 14, 16, 18, 20, 22, 24 to the surface of the pipe at locations axially transverse of heater 12.

It is preferred that the pipe axis 26 be relatively horizontal for purposes of this invention for reasons which may be understood from the following description. But at the outset it should be recognized that the inventive concept is based on heat transfer characteristics of both fluids and solids and it also involves heat transfer by conduction, convection and radiation under static, laminar and turbulent flow conditions. Where the axis 26 deviates to some great degree from horizontal, the convection cells generated inside the pipeline may distort the temperature patterns and heat transfer data because of gravity, among other things.

It is preferred that the vertically aligned location of sensing devices 14, 16, 18 and 20, 22, 24 be axially spaced from the heat source 12 by from 2 to 25 inches and most preferably from 3 to 8 inches.

The first determination to be made is whether the fluid inside pipe 10 is liquid or gaseous. This is accomplished by measuring the temperature sidewall at, for example, sensor 16 before controller 28 activates the power source 30 to begin the generation of heat by heater 12. The magnitude of heat from power source 30 to heater 12 is controlled by controller 28 through power meter 32. Then the heater is activated.

After a short period of time, preferably 3 to 30 minutes and most preferably about 5 minutes, a second reading is taken by temperature device 16. Where there is no substantial change in temperature between the first reading and the second reading at device 16, one can conclude that the contents of the pipe 10 is a liquid. This conclusion may be drawn from the fact that a comparatively dense liquid is a sufficient heat sink as to transfer almost all of the heat from heater 12 to the liquid without a transverse longitudinal flow. The distance from heater 12 to temperature sensor 16 is 50 or 100 times greater than the thickness of the pipe wall to the liquid. On the other hand, if within the specified period of time, the temperature at sensor 16 has increased, it may be concluded that the contents of the pipe is a gas. This conclusion may be drawn from the fact that a comparatively less dense gas is unable, because of its density and low thermal conductivity, to extract all of the heat from the pipe wall generated by the heater 12.

The next consideration is to determine whether or not there is fluid flow within pipe 10 and if so, what direction the fluid is flowing. Indeed, the data generated early on will probably be simultaneous with the determination of the liquid-gas issue. It involves taking temperature readings upstream and downstream of heater 12. For example, temperature sensors 16 and 22 mounted on the sidewall about 90° down from the top of the pipe are located such that a line drawn between sensor 16 and sensor 22 is approximately parallel with pipe axis 26. That line passes from one sensor through the heat source to the other sensor. Sensor 16 and sensor 22 are spaced equidistant from heater 12.

Figure 2:
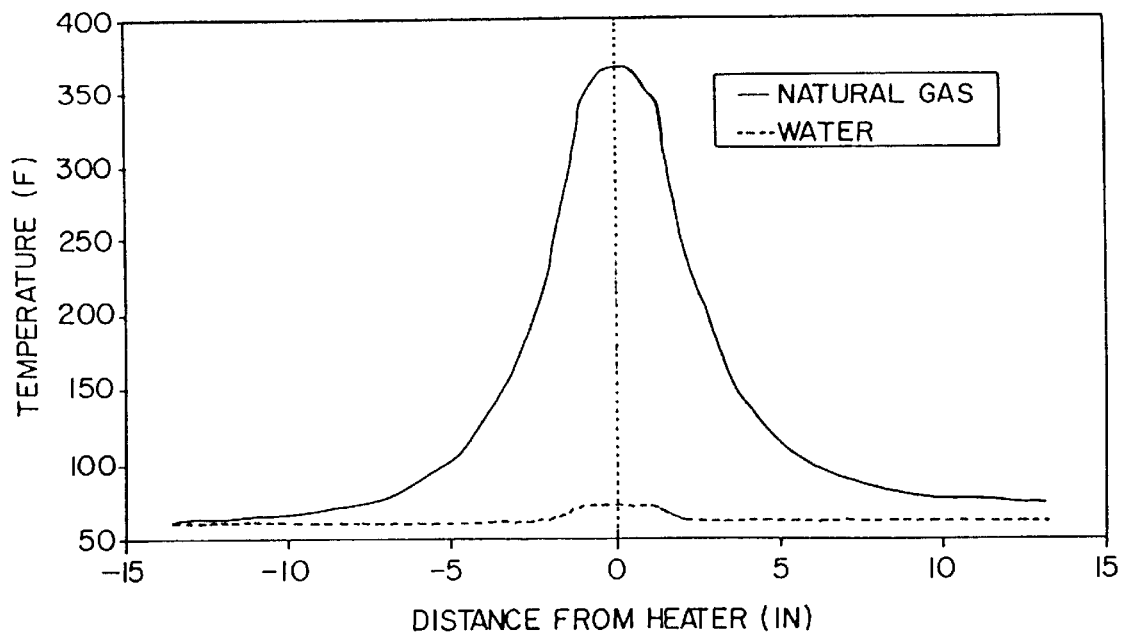
FIG. 2 is a chart of sidewall temperatures for natural gas and water-filled pipes with a flow velocity of 6 ft/sec. and a pressure of 140 psia.
Figure 4:
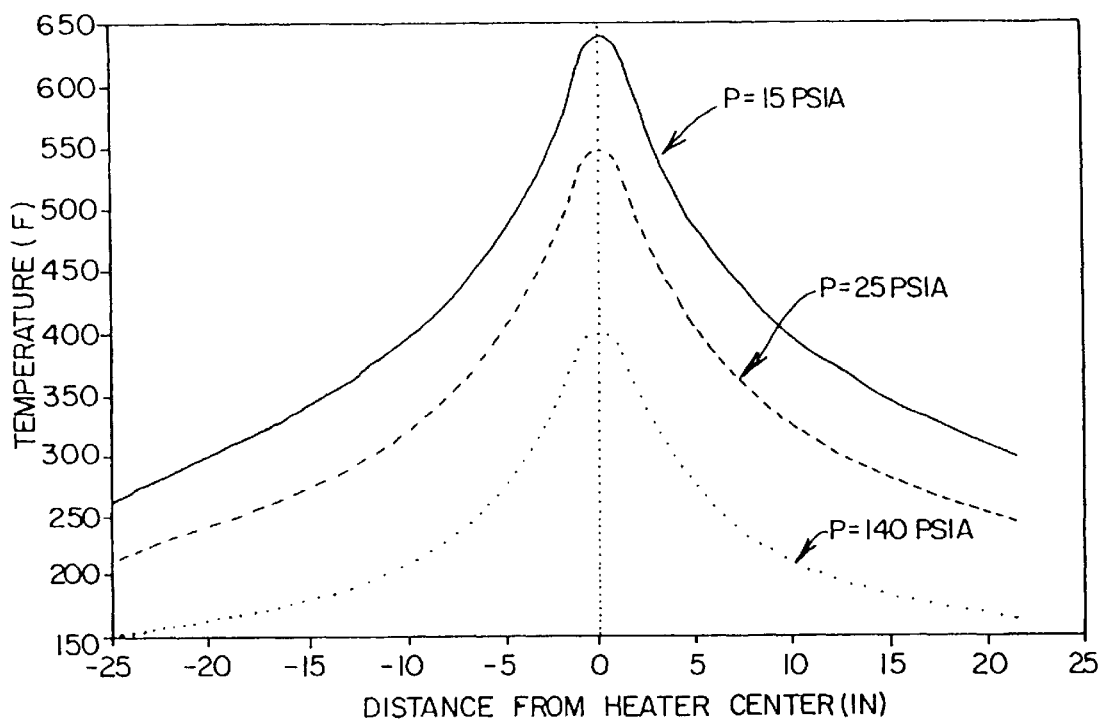
FIG. 4 is a chart of calculated, projected sidewall temperatures of a pipe with static gaseous contents at various pressures.

An observation of FIGS. 2 and 4 will help illustrate the conclusions which may be drawn from data generated from sensors 16 and 22. It is intuitive that a temperature pattern of liquid or gas in a pipeline heated according to FIG. 4 would have a plotted temperature pattern defining a classic bell-shaped curve. The bell-shaped curve for the liquid as seen in FIG. 2 is much flatter than the one for gas because of the greater ability of the dense liquid to absorb heat. Accordingly, a proper reading after a short period of time, both upstream and downstream of heater 12, confirms whether the contents are liquid or gaseous. If the contents are liquid and static, the temperatures at 16 and 22 should read about the same and not greatly different from the temperature reading at the heat source, see FIG. 2. On the other hand, where the contents are gaseous, the temperature at heater 12 is substantially greater than the temperature readings at 16 and 22 and the readings at 16 and 22 are elevated as compared to the initial reading before the controller 28 is activated.

FIG. 2 is a plot of temperatures taken at sidewall locations about 90° down the side of the pipe at locations 5, 10, and 15 inches upstream and downstream of heater 12. In the illustrated curves, the pipe was 6 inches in diameter with fluid contents having a velocity of 6 ft/sec. and a pressure of 140 psia for both natural gas and water. The temperatures plotted are at steady state after 1½ hours of heating.

A couple of things should be mentioned at this point which could have an effect on some of the readings. The locations of temperature sensors 14 and 24 are at the top of the pipe. Readings only at the top of a pipe may be misleading because pipes do not run full of liquid as a general rule. There may be a small trough of air at the top of a water-filled pipe which could give misleading data.

A reading of the temperatures at the sidewall locations 16, 22 and an observation of FIG. 2 will show the direction of flow of the flowing gas. Observe that the temperature pattern of the natural gas is slightly skewed to the right indicating that the gas is flowing from left to right. The temperatures at 5, 10 and 15 inches to the right of the heater are slightly higher than the temperatures of the gas at 5, 10 and 15 inches to the left of the heater. The pattern of temperatures for water is not so clear-cut because of its greater thermal conductivity.

These data have established whether the pipe is filled with gas or liquid and whether it is static or flowing if it is gas. Further, the data allows one to determine the direction of flow of the flowing gas, if it is flowing. This information may be enough for the excavation crew to determine that they have not located the desired pipe. If that is the case, it is very important.

Figure 3:
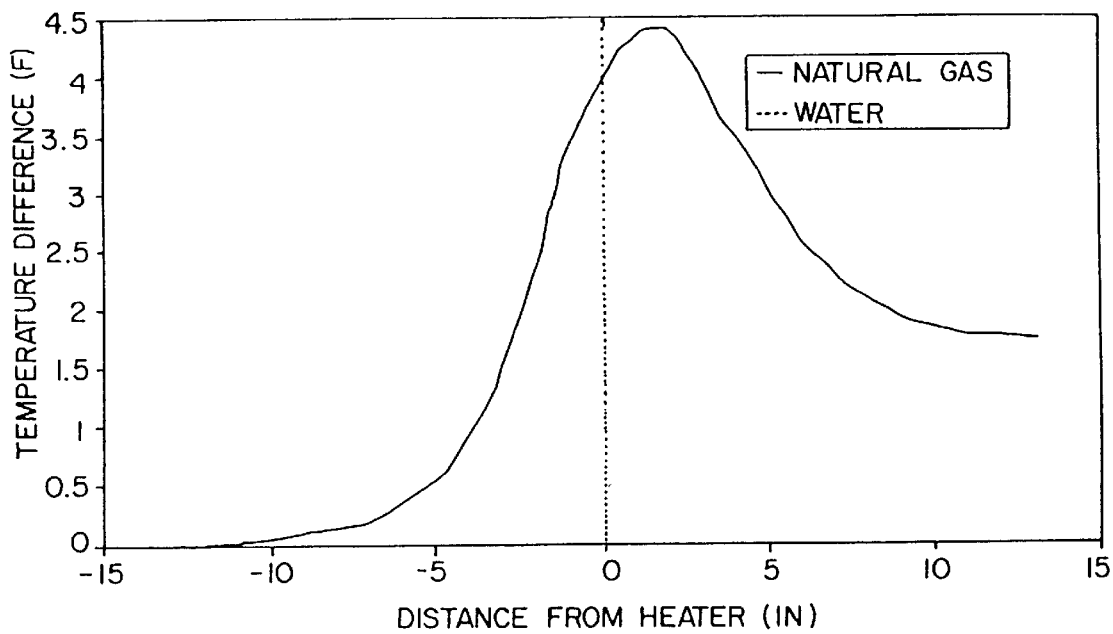
FIG. 3 is a chart of temperature differentials between the top and bottom of a pipe under the same conditions as the fluids in FIG. 2.

An observation of FIG. 3 shows an interesting technique useful for gaseous flow but of no significance at all to liquid flow. It is that a reading of temperature differentials between the top and bottom of the pipe can give some very useful information. The curve in FIG. 3 is for natural gas and it is shows the temperature difference between readings of the sensors at the top of the pipe, at 14 and 24, as compared to readings at the bottom of the pipe, at 18 and 20. This data in FIG. 3 was generated from natural gas flowing in a 6 inch diameter pipe at a velocity of 6 ft/sec. and at a pressure of 140 psia.

It will also be observed in FIG. 1 that an insulated clam-shell device or jacket 34 surrounds the pipe 10 and the apparatus mounted on the pipe wall. This preserves the heat generated by heater 12. Insulation of and screening from the environment is intended to mitigate against temperature differentials between the pipe excavated in Wisconsin in January and one excavated in the Mojave Desert in July. The intent is to have the heat generated by heater 12 as the only heat generating device in the test area.

Figure 5:
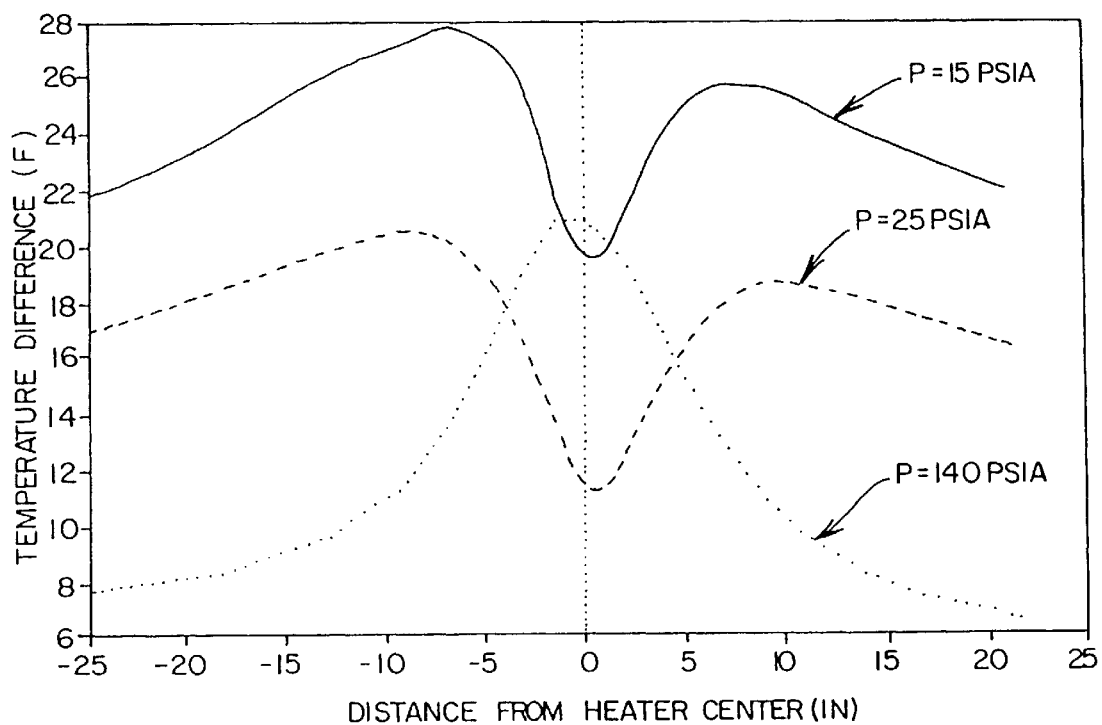
FIG. 5 is a chart of calculated, projected top-to-bottom temperature differences of a pipe with static gaseous contents at various pressures.
Figure 6:
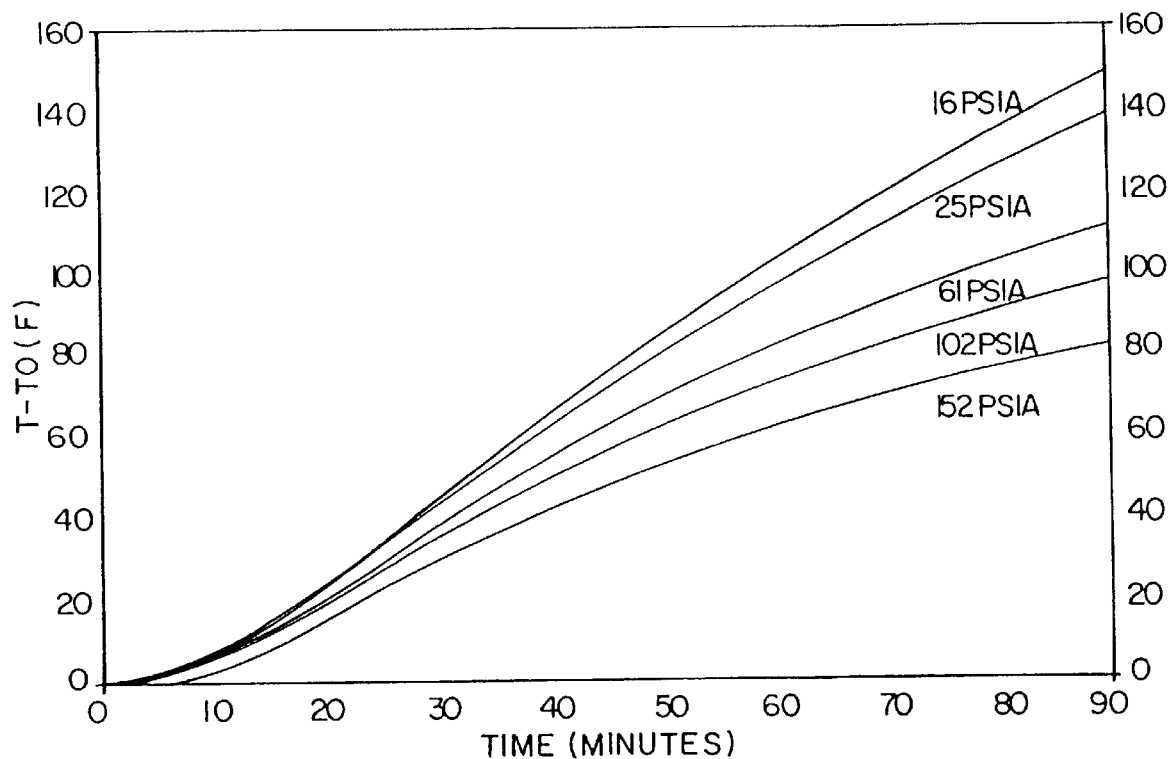
FIG. 6 is a chart of observed experimental temperature rise with a ring heater in a pipe with static gaseous contents versus time at a location about 5 inches from the centerline of the 250 W heat source.
Figure 7:
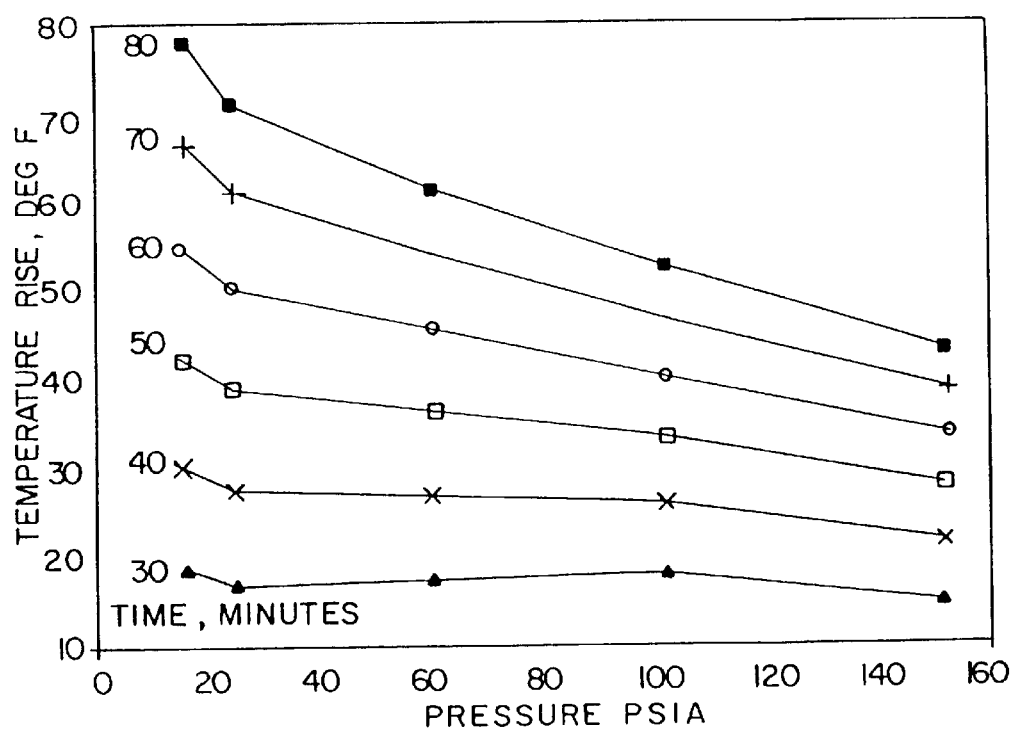
FIG. 7 is a chart providing an alternative plot of the same data as FIG. 6 but with the axes defining temperature rise versus pressure.

FIG. 4 illustrates the symmetric steady state profile of different pressures plotted for distance from the center of the heater after a period of about 90 minutes or longer. With this information available for comparison based on a reading at a location transverse to the heater, one can predict the pressure of the static gas inside a pipe because the temperature and distance are known. Similar information can be derived from the chart illustrated in FIG. 5. FIGS. 4 and 5 are based on static conditions in relatively ideal conditions and in field operations the excavation crew does not have enough time to allow the excavated pipe to come to steady state conditions. Accordingly, an alternative set of parameters is illustrated in FIGS. 6 and 7 which may be used in the field more readily. The data illustrated in FIG. 6 is intuitive in that the fastest temperature rise is at the 16 psia pressure and the slowest rise is the 152 psia pressure. It is intuitive because it is to be expected that greater amounts of heat would transfer in the denser gas at the higher pressure. Accordingly, the temperature does not rise as quickly.

FIG. 7 shows six curves plotted at 30, 40, 50, 60, 70 and 80 minutes after the onset of temperature rise at a location 10 inches from the centerline of the heater 12. This allows an estimate of the pressure because the excavation crew will know the period of time and the temperature. This can be translated into an estimate of pressure using FIG. 7. Unfortunately, the time involved is burdensome. Note that the curve at 30 minutes is essentially a flat curve making it very difficult to give a reasonable estimate as to the internal gas pressure. On the other hand, at 80 minutes the curve is much better because of its change in slope as pressure increases.

FIG. 6 shows the temperature rise in the sidewall of the pipe measured 5 inches downstream from a ring heater with a 250 W heat input.

Figure 8:
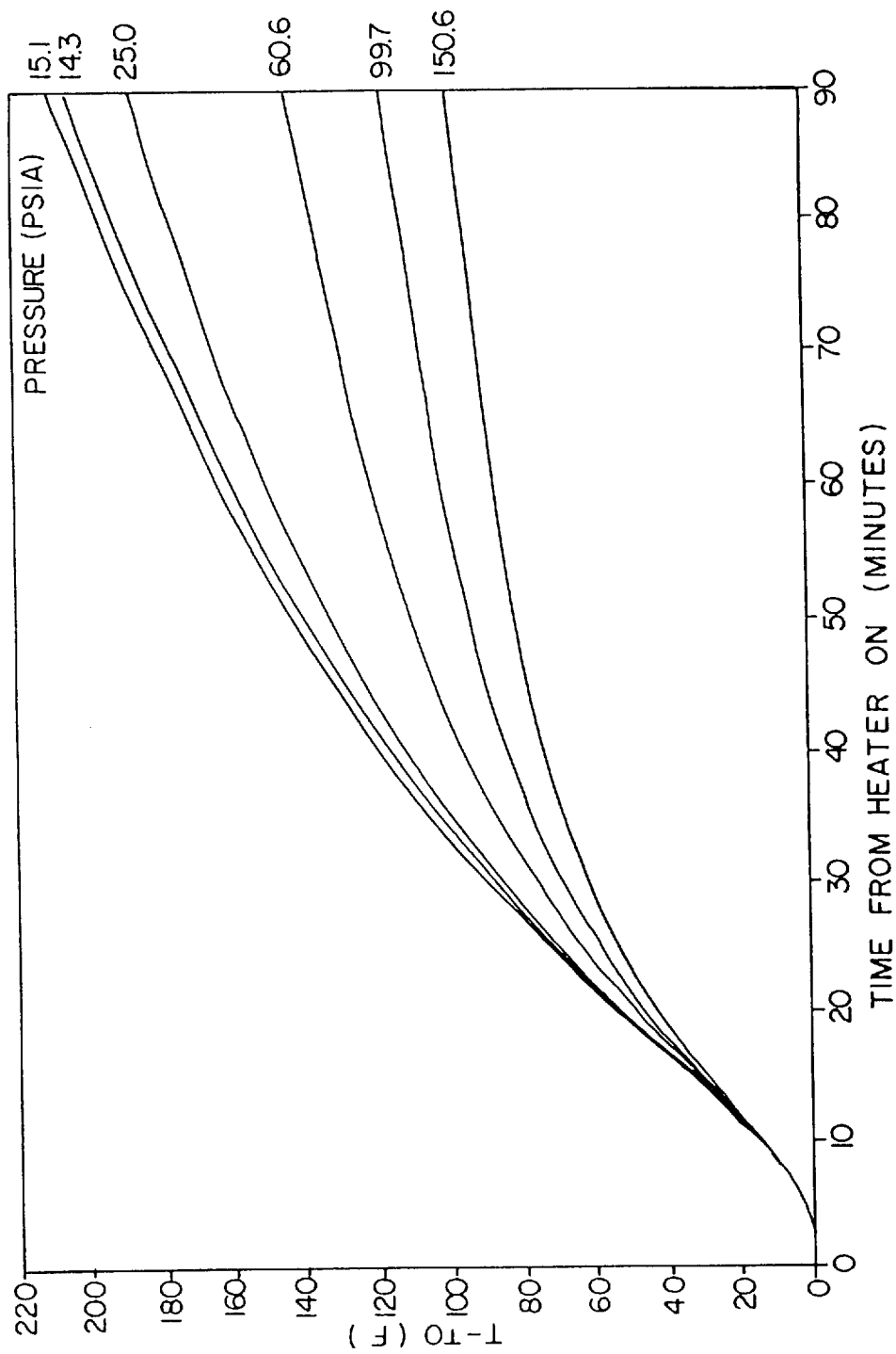
FIG. 8 is similar to FIG. 6 except that it is a plot of observed experimental data with a heater input of 250 W taken at a point 6 inches from the centerline of the heater.

FIG. 8 has the same location with slightly different pressures using a patch heater with a 250 W heat input and measured 6 inches downstream from the center of the heater 12.

Both systems were operating at 250 W. The ring heater distributes the heat over a wider area so that the heat flux and overall temperatures are much lower under the heater compared with the patch heater which delivers the same power to a much smaller area. The local higher temperatures might set up stronger convection currents inside the pipe so that the temperatures rise faster for the patch heater system.

The heat flow method relies on the normal response of the pipe wall to a heat input. The peak wall temperature occurs directly under the heater. For the purpose of estimating pressure, the heat input should be as high as possible, which implies the wall temperature under the heater will be very high, but there is an upper limit to the temperature determined by the metallurgy of the pipe. From other data it has been determined that a safe upper limit is about 800° F.

Figure 9:
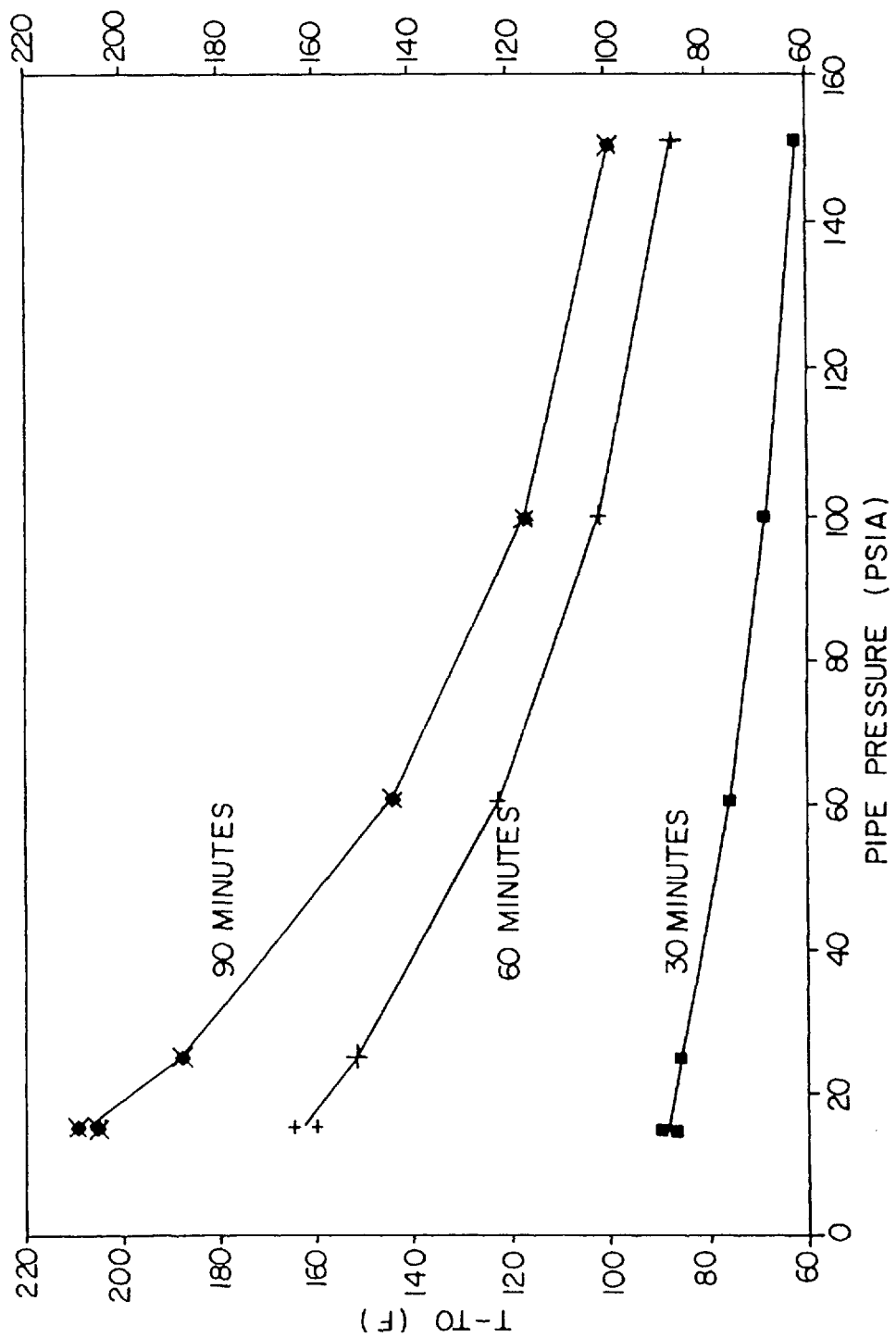
FIG. 9 is a chart similar to FIG. 7 except that it is an alternative plot of patch heater experimental data with a heater input of 250 W and readings taken 6 inches from the centerline of the heater.

The data from FIGS. 6 and 8 are used to produce the curves shown in FIGS. 7 and 9. The curves are plots of temperature rise as a function of pressure. As seen in FIG. 9, the slopes of the curves are greater for the patch heater than for the ring heater as illustrated in FIG. 7. The 30 minute curve from the patch heater has a reasonable slope to permit an estimate of pressure to be made. The slope of the curve for 60 minutes is even steeper. Therefore, an operator at the excavation site can obtain a rough estimate at 30 minutes and perhaps elect to wait another 30 minutes for a better estimate. This is not the case with the ring heater based on curves in FIG. 7, an operator would have to wait at least 50 minutes to get even a reasonably rough estimate from the ring heater system. Therefore, the patch heater does provide a more effective and accurate system while improving the field applicability.

Figure 10:
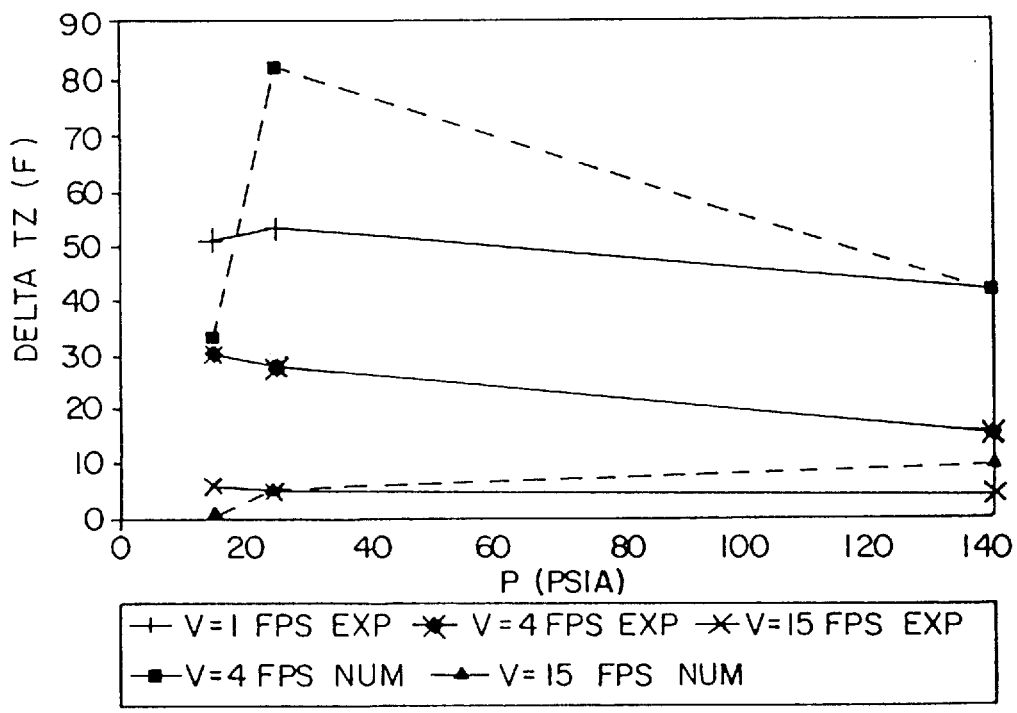
FIG. 10 is a chart showing calculated and experimental data of a plot of top-to-bottom temperature differences versus pressure with flowing gas at various velocities with temperature reading 10 inches downstream from the centerline of a ring heater.

FIG. 10 is more helpful in this context. It is a plot of temperature difference as a function of pressure at 10 inches downstream of the centerline of a ring heater having a 250 W heat input. There is a fairly good correlation between the numerical analysis (num) and the experimental results actually measured (exp) and it is significant because the correlation has so little to do with pressure and it is controlled almost completely by velocity. It was intuitively expected that the top-to-bottom temperature differences would reflect pressure differences due to the varying strength of the free convection cells generated in the pipe during the heating process. However, both the numerical predictions and the experimental results show that the main influence on the top-to-bottom temperature difference is from velocity. Thus, the top-to-bottom temperature difference is a good indicator of velocity. Thus, the downstream top-to-bottom temperature measurement yields a good estimate of gas velocity which is nearly independent of pressure.

The data being discussed at this point relates to the ring heater but it may be freely extrapolated to the patch heater for purposes of this discussion.

Figure 11:
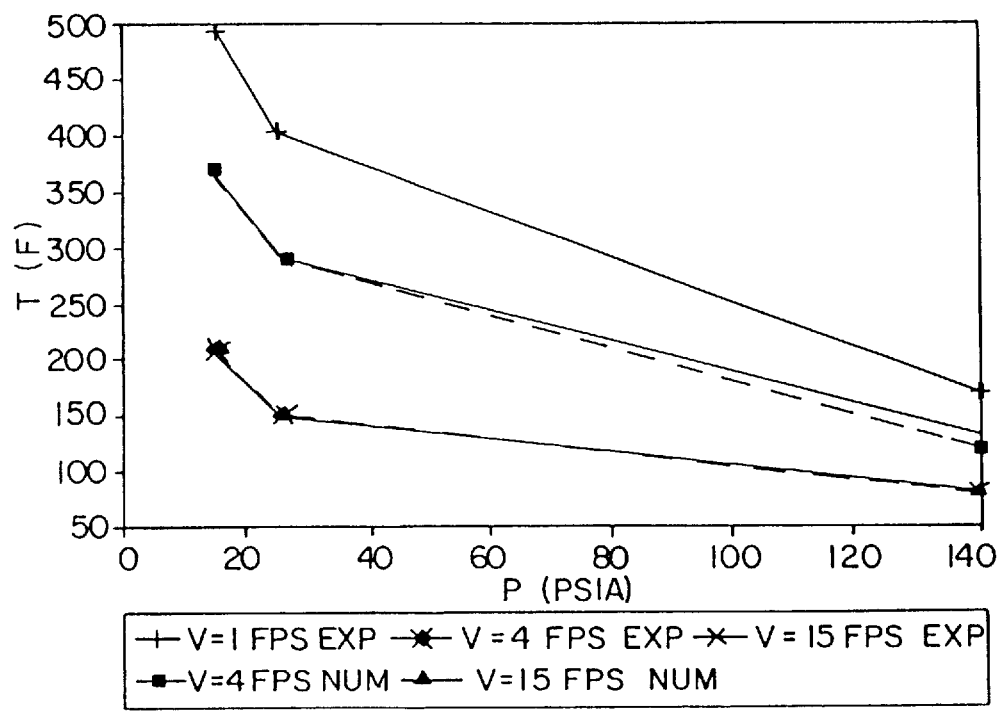
FIG. 11 is a chart showing calculated and experimental data of a plot of the sidewall temperature differences versus pressure for various flow rates for gas with temperature readings 10 inches downstream from the centerline of the heater.

Once the approximate velocity of the gas is known (from FIG. 10), the pipe sidewall temperature proves to be indicative as can be ascertained from the data in FIG. 11. Those data show that there is excellent agreement between numerical predictions and experimental data. They also show that the measurement is more sensitive at low velocities. That is, the slope is steeper, which is expected and advantageous for differentiating between low pressure ranges.

The experimental and numerical results of FIG. 11 both demonstrate that a pressure estimate can be obtained from the top-to-bottom temperature difference and the sidewall temperature. First, the temperature difference is used to obtain an estimate of velocity from FIG. 10. Then, the data from FIG. 10 using the velocity is used in FIG. 11 to determine the correlation between sidewall temperature 10 inches downstream from the centerline of the heater and the internal pressure read on the X axis of FIG. 11. The measured sidewall temperature is used to estimate the pressure.

A major goal of this invention is to estimate pressure within 30 minutes under flowing gas conditions. Unfortunately, as illustrated in FIG. 9, the period of time to reach near steady state exceeds this 30 minute time period.

Because the patch heater proved to be an effective technique for estimating pressures of static gas, the patch heater has been tested under flowing gas conditions. It was necessary to get some estimate of pressure and velocity within a 30 minute period without waiting for steady state temperatures. Accordingly, work was done to obtain an estimate using the temperature difference between the top and bottom of the pipe downstream of the heater.

Figure 12:
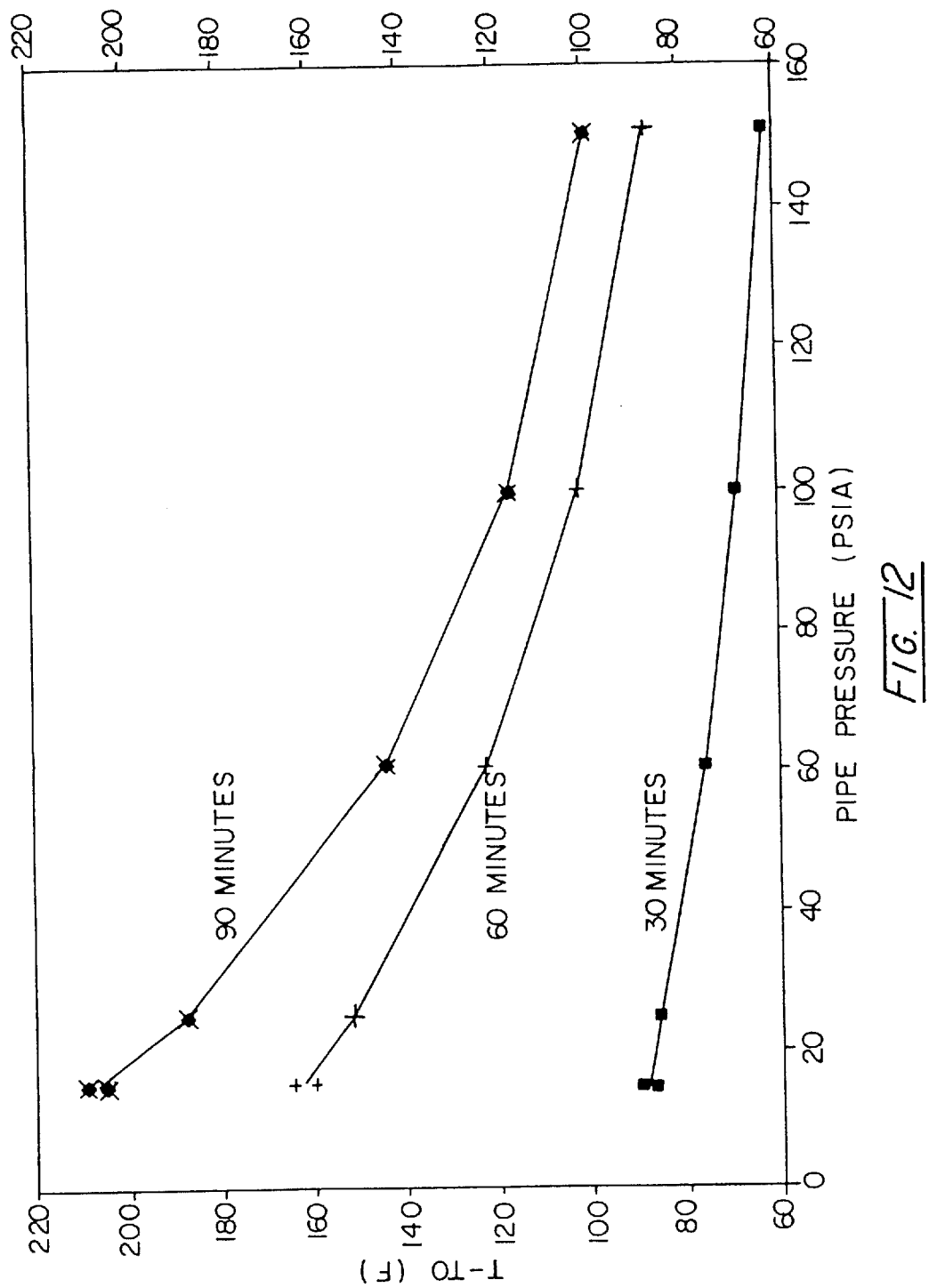
FIG. 12 is a chart of the rate of rise of top-to-bottom temperature difference versus time in a 4 inch pipe with readings taken at 6 inches downstream of the centerline of a patch heater for various pressures at a velocity of 4 ft/sec.
Figure 13:
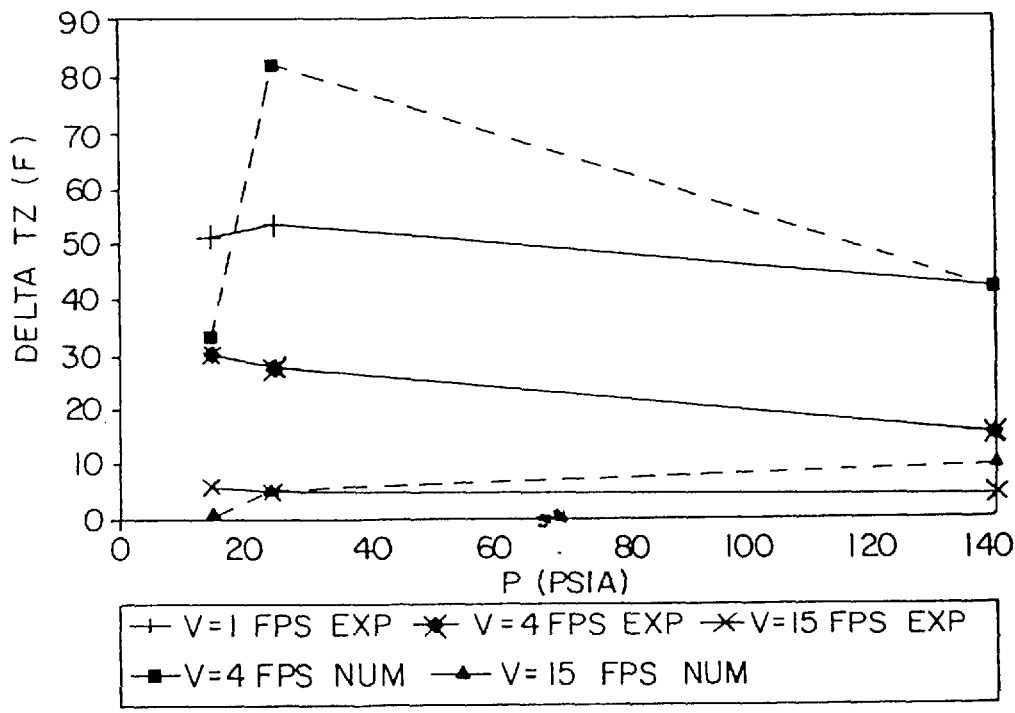
FIG. 13 is a chart of the rate of rise of temperature of a patch heater measured at the sidewall of a pipe at a point 6 inches downstream from the centerline of the heater, plotted for various pressures with a flow rate of 4 ft/sec. versus time.

FIG. 12 is a plot of the rate of temperature rise measured in a 4 inch pipe 6 inches downstream of the patch heater (dTz denotes the top-to-bottom temperature difference downstream of the heater). The rate of rise of both dTz and the steady state value of the sidewall temperature downstream of the heater at the same location for all the cases of pressure are plotted as a function of time in FIGS. 12 and 13 for a nominal gas velocity of 4 ft/sec. Note that the peaks in the rate occur in under 30 minutes. The behavior of the peaks with respect to time appear to follow power laws with pressure, P, and velocity, V. Thus, the data for heights were modeled with a relatively simple relation given by $$H = CP^a V^b \quad \text{(Eq. 1)}$$

, where a, b, C are parameters that are determined by the data.

The form of the relation is particularly useful because the estimates of the constants can be found using a multiple linear regression by taking the logarithms of both sides. That is $$a\ log(P) + b\ log(V) + log(C) = log(H) \quad \text{(Eq. 2)}$$

, where log(P), log(V), and log(H) are now the X, Y, and Z variables, a and b are slopes, and log(C) is the intercept. Thus, a well-known commercial spreadsheet computer program can be used to obtain the estimates of a, b, and C and need not be discussed in detail.

Two sets of data were used to obtain estimates of pressure and velocity. The first set did not include the static cases, and the second set did. For static gas the velocity equals zero, and the logarithmic approach breaks down. Therefore, when the regression was applied to the set with the static data, V was replaced with V+1. The offset term of 1 was arbitrarily chosen, but was deemed appropriate since the lowest value of flowing gas used in the experiments was one ft/sec. If this power law is kept for the engineering evaluation unit, then the offset term could also be chosen with an optimization approach.

Figure 14:
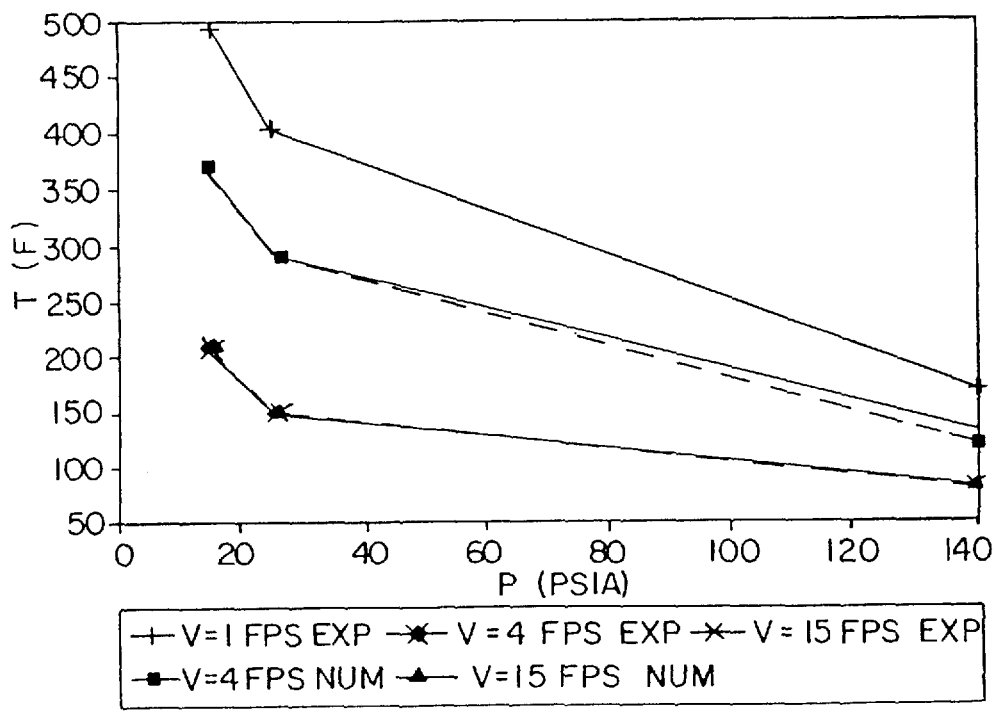
FIG. 14 is a plot of estimated versus actual pressures with FIGS. 12 and 13 parameters.
Figure 15:
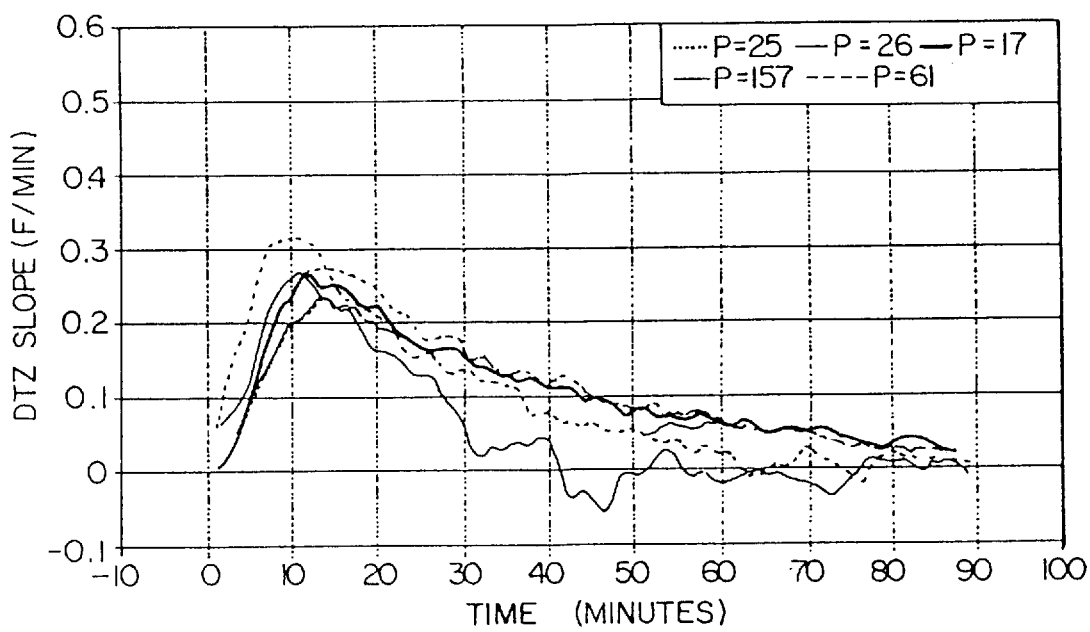
FIG. 15 is a plot of estimated versus actual velocities with FIGS. 12 and 13 parameters.

The results of the regression analysis are the estimates of the parameters, a, b, and C. The power laws are manipulated to yield estimates of pressure and velocity given the peaks heights using the estimates of the parameters. The results for the data set without the static cases are shown in FIGS. 14 and 15. They are plots of the estimates of pressure and velocity versus the measured values of pressure and velocity. As seen in these figures, acceptable performance is obtained for both the estimates of velocity and pressure.

Power law regressions to obtain estimates in under 30 minutes are as follows:

Pressure Estimate Without V=0 Data $$\hat{P} = 2875\ H_h^{-3.278} H_{\Delta T_z}^{0.9277} \quad \text{(Eq. 3)}$$

Pressure Estimate With V=0 Data $$\hat{P} = 6310\ H_h^{-3.824} H_{\Delta T_z}^{1.318} \quad \text{(Eq. 4)}$$

Velocity Estimate Without V=0 Data and Without Pressure Estimate $$\hat{V} = 0.1177\ H_{\Delta T_z}^{-2.700} \quad \text{(Eq. 5)}$$

Velocity Estimate Without V=0 Data and Using Pressure Estimate $$\hat{V} = 0.07481\ H_{\Delta T_z}^{-2.522}\ \hat{P}^{0.1706} \quad \text{(Eq. 6)}$$

Velocity Estimate With V=0 Data and Without Pressure Estimate $$\hat{V} = 0.4170\ H_{\Delta T_z}^{-1.982} - 1 \quad \text{(Eq. 7)}$$

Velocity Estimate With V=0 Data and Using Pressure Estimate $$\hat{V} = 0.1748\ H_{\Delta T_z}^{-1.821}\ \hat{P}^{0.2600} - 1 \quad \text{(Eq. 8)}$$

It has been shown that the heat flow method works with both a ring heater and a patch heater. The patch heater is expected to be much easier to use in the field so it is the preferred implementation. Both heaters are resistive heaters. Direct contact heaters are preferred at this time because of their ease of use and inexpensive cost as opposed to induction heaters or radiant heaters. In the experiments indicated above, thermocouples were used as temperature sensors but any temperature-measuring devices may be used. An observation of FIG. 1 will show that all of the temperature-sensing devices, including the one directly under patch heater 12, are directly connected to the data acquisition system and computer 36 used by the on-site excavation crew to make the determination on whether or not they have excavated the correct pipe. The data display associated with the system 36 may be in the form of numbers, charts, or whatever works.

One function of the temperature-sensing device beneath patch 12 is to ensure that the temperature does not exceed 800° F. where the metallurgy of the steel pipe could be irreversibly changed.

The heat flow method requires that the heater 12 be given a fixed amount of power for a given test. The computer 36 selects the power level for the size of the pipe being evaluated and uses this level as the set point for the controller 28. Its output controls and SCR circuit 30 delivers power to the heater. A power meter 32 monitors the electrical power and feeds the value back to the controller 28. FIG. 1 illustrates the controller 28 as an individual unit. It could be implemented in the computer software and interfaced with the hardware through the data acquisition system 36.

In summary, the procedural steps for making the appropriate determination useful in the field are as follows:

Liquid-Filled Versus Gas-Filled

First measure the nominal pipe wall temperature, and then turn on the heater 12. After 10 minutes, check that the downstream (or upstream) temperatures at 22 are significantly different from zero. If the temperature rise is not at least 5° F. and the top-to-bottom temperature difference at 20 and 24 is approximately zero, then the pipe is liquid-filled. If the temperature rise is greater than 5° F. or the top-to-bottom temperature difference is greater than zero, then the line is gas-filled.

Flowing Versus Static Gas

After 20 minutes has passed, compare the upstream at 16 and downstream temperatures at 22. If they are equal (within ±5° F.), the gas is static. If the downstream temperature is at least 5° F. greater than the upstream temperature, then gas is flowing. The direction of flow is from the lower temperature to the higher temperature. Use the appropriate procedure below to estimate gas pressure.

Pressure Estimate for Static Gas

After 30 minutes measure the downstream sidewall temperature at 22. Use the correlation in FIG. 11 for 30 minutes to estimate pressure from temperature. If the pressure is near a boundary that separates the ranges that define operational procedures, the operator may wish to allow the pressure measurement to proceed. After 40 minutes, measure the sidewall temperature and estimate pressure using the correlation for 40 minutes.

Pressure Estimate For Flowing Gas

Within 30 minutes the rate of temperature rise should have peaked and have begun to tail off. Measure the peak heights in the rates of rise of the downstream sidewall and the temperature, $T_h$, of FIG. 13, and the downstream top-to-bottom temperature difference, $\Delta T_z$, FIG. 12. The regressions stated above are then used to calculate estimates of both pressure and velocity.

Having thus described the invention in its preferred embodiment, it will be clear that modifications may be made to the apparatus and the procedure for mounting the same without departing from the spirit of the invention. It is not the intention of the inventors to limit the invention by the drawings, nor the words used to describe the same. Rather it is intended that the invention be limited only by the scope of the appended claims.

We claim:

1. In combination, a pipe of unknown volume partially encompassed by a housing, said pipe containing an unknown fluid of unknown composition and unknown pressure, said fluid being selected from the group consisting of a flowing fluid and a static fluid, said fluid also being selected from the group consisting of a gaseous fluid and a liquid fluid, the combination including (1) a heater attached to the external surface of the pipe within the housing, (2) a source of electrical energy connected to said heater through a controller for controlling the energy to said heater, (3) a plurality of temperature sensors attached to the surface of said pipe inside said housing, and (4) said sensors being connected to a screen of a data display system outside said housing for displaying temperatures from said sensors, said plurality of temperature sensors including a first set of three temperature sensors on the pipe surface in a first direction transverse to the heater, and a second set of three temperature sensors on the pipe surface in a second direction transverse to the heater and opposite to the first direction, each set including one sensor on the top of the pipe, one sensor about half way down the side of the pipe, and one sensor on the bottom of the pipe.

2. The combination of claim 2 including an additional temperature sensor attached to the pipe surface at the heater, said temperature sensor at said heater being connected to said controller to regulate the energy delivered to said heater such that the pipe surface at said heater does not exceed a pre-set temperature.

3. The combination of claim 2 further including charts of temperatures in pipes of known gases at known pressures and known flow rates for comparison with said screen of data display system.

4. The combination of claim 1 further including charts of temperatures in pipes of known gases at known pressures and known flow rates for comparison with said screen of data display system.

* * * * *

UNITED STATES PATENT AND TRADEMARK OFFICE
CERTIFICATE OF CORRECTION

PATENT NO. : 5,836,693
DATED : November 17, 1998
INVENTOR(S) : Stulen et al.

It is certified that error appears in the above-indentified patent and that said Letters Patent is hereby corrected as shown below:

Claim 2, line 1, delete "2" and insert therefor --1--.

Signed and Sealed this

Twenty-third Day of March, 1999

Attest:

Q. TODD DICKINSON

Attesting Officer

Acting Commissioner of Patents and Trademarks